United States Patent [19]
Lok et al.

[11] Patent Number: 5,912,111
[45] Date of Patent: Jun. 15, 1999

[54] GOLD(I) SENSITIZERS FOR SILVER HALIDE EMULSIONS

[75] Inventors: Roger Lok, Rochester; Weimar W. White, Canaseraga; Melanie W. Marshall, Webster, all of N.Y.

[73] Assignee: Eastman Kodak Company, Rochester, N.Y.

[21] Appl. No.: 09/025,188

[22] Filed: Feb. 18, 1998

[51] Int. Cl.$^6$ .................. G03C 1/09; C07F 1/12
[52] U.S. Cl. .......... 430/603; 430/605; 430/567; 430/569; 556/113
[58] Field of Search .................. 430/603, 567, 430/605, 569; 556/113

[56] References Cited

U.S. PATENT DOCUMENTS

| | | | |
|---|---|---|---|
| 3,503,749 | 3/1970 | Tavernier et al. | 430/605 |
| 4,284,717 | 8/1981 | Toya et al. | 430/603 |
| 5,015,567 | 5/1991 | Suga et al. | 430/603 |
| 5,049,484 | 9/1991 | Deaton | 430/605 |
| 5,220,030 | 6/1993 | Deaton | 548/105 |
| 5,252,455 | 10/1993 | Deaton | 430/605 |
| 5,391,727 | 2/1995 | Deaton | 540/1 |
| 5,620,841 | 4/1997 | Lok et al. | 430/600 |
| 5,686,236 | 11/1997 | Lok et al. | 430/600 |
| 5,700,631 | 12/1997 | Lok et al. | 430/603 |

OTHER PUBLICATIONS

Japanese Abstract No. 8069075 A, Derwent Info. Ltd.

*Primary Examiner*—Mark F. Huff
*Attorney, Agent, or Firm*—Sarah Meeks Roberts

[57] ABSTRACT

This invention relates to a silver halide photographic element comprising a support and a silver halide emulsion layer, the emulsion layer comprising a Au(I) compound having the formula

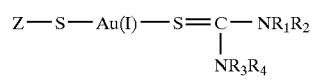

wherein Z is a substituted or unsubstituted alkyl, aryl, alkylaryl, or heterocyclic group; and $R_1$, $R_2$, $R_3$ and $R_4$ are independently substituted or unsubstituted alkyl, aryl, alkylaryl, or heterocyclic groups, or one or both of $R_1$ and $R_2$ or $R_3$ and $R_4$, may independently combine to form a nitrogen containing ring with the nitrogen to which they are attached.

30 Claims, No Drawings

GOLD(I) SENSITIZERS FOR SILVER HALIDE EMULSIONS

FIELD OF THE INVENTION

This invention relates to novel Au(I) sensitizers and their use in silver halide photographic elements. It further relates to a method of sensitizing silver halide emulsions with such Au(I) sensitizers.

BACKGROUND OF THE INVENTION

There has been considerable effort devoted to improving the sensitivity of silver halide crystals to actinic radiation and thereby increasing the sensitivity of the photographic elements in which they are contained. In this regard, photographic chemists have attempted to vary the components of, or the processes for making, silver halide emulsions. One particularly preferred means to improve sensitivity has been to chemically sensitize photographic emulsions with one or more compounds containing labile atoms of gold, sulfur, selenium or the like. Examples of chemically sensitized photographic silver halide emulsion layers are described in, for example, *Research Disclosure*, Item No. 308119, December 1989, Section III, and the references listed therein. (*Research Disclosure* is published by Kenneth Mason Publications Ltd, Dudley Annex, 12a North Street, Emsworth, Hampshire PO 10 7DQ, England.)

Many gold sensitizers have been described. For example, U.S. Pat. No. 3,503,749 describes the use of water soluble Au(I) thiolate salts comprising one Au atom ligated to one sulfur containing ligand; U.S. Pat. No. 5,220,030 teaches the use of Au(I) compounds with bis mesoionic heterocycles; U.S. Pat. No. 5,252,455 and U.S. Pat. No. 5,391,727 disclose the use of Au(I) macrocyclic cationic sensitizers; U.S. Pat. No. 5,049,484 teaches the use of Au(I) sensitizers having a Au atom ligated to the nitrogen atom of heterocyclic rings. U.S. Pat. No. 5,620,841 discloses the use of gelatin dispersions of a Au(I) thiosulfonato sensitizer with two different ligands at least one of which is mesoionic; and U.S. Ser. No. 08/672,254 teaches the use of gelatin dispersions of Au(I) thiosulfonato sensitizers with two different ligands at least one of which is a thioether group. JP 8069075 discusses the use of organic gold sulfide compounds in the sensitization to give low fogging and high contrast silver halide photographic materials. However, all of the above compounds have one or more disadvantages such as difficulty of synthesis or poor stability.

One common chemical sensitizer used in the sensitization of silver halide emulsions is aurous sulfide which is made as a colloidal gelatin dispersion, the exact composition of which is not well characterized. This gold sulfide dispersion can give rise to lot-to-lot variability and undesirable and inconsistent sensitometric performance. The source of this variability may come from side reactions in the preparation of this highly insoluble solid since these reactions produce species which may be photographically active.

The bis Au(I) mesoionic heterocycles e.g. bis(l,4,5-trimethyl-1,2,4-triazolium-3-thiolate) gold (I) tetrafluoroborate, TTT, while being very useful sensitizers, are somewhat lacking in solution stability. Further, for the mesoionic triazolium sensitizers, multiple steps and recrystallizations are required in the preparation of the starting material bis(tetramethylthiourea) Au(I) tetrafluoroborate. Synthesis of the gold ligand 1,4,5-trimethyl-1,2,4-triazolium-3-thiolate is difficult, and the preparation of the mesoionic triazolium sensitizer is limited to small batches.

Thus, there is still need for effective Au (I) compounds that are stable and easily manufactured from readily available starting materials.

SUMMARY OF THE INVENTION

This invention provides compounds of the formula

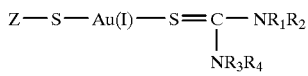

wherein Z is a substituted or unsubstituted alkyl, aryl, alkylaryl, or heterocyclic group; and $R_1$, $R_2$, $R_3$ and $R_4$ are independently substituted or unsubstituted alkyl, aryl, alkylaryl, or heterocyclic groups, or $R_1$ and $R_2$, and $R_3$ and $R_4$, may independently combine to form a nitrogen containing ring with the nitrogen to which they are attached. It further provides a silver halide photographic element comprising a support and a silver halide emulsion layer, the emulsion layer comprising said Au(I) compound.

This invention also provides a silver halide photographic element comprising a support and a silver halide emulsion layer, the emulsion layer having been chemically sensitized in the presence of an Au(I) compound having the above formula; and it provides a method of preparing a silver halide emulsion comprising precipitating silver halide grains in an aqueous colloidal medium to form an emulsion, heating the emulsion, and adding to the emulsion, either before or during heating, an Au(I) compound of the above formula.

The novel Au(I) compounds of the present invention are highly effective sensitizers for silver halide emulsions. The synthesis of the compounds employs inexpensive and commercially available starting materials and the ease of preparation reduces the cost of manufacturing of the silver halide photographic element. Further, the preparation of the gold compounds of the present invention avoids the use of explosive gold fulminates.

DETAILED DESCRIPTION OF THE INVENTION

The Au(I) compounds of this invention are represented by the formula:

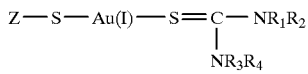

wherein Z represents an alkyl, aryl, alkylaryl, or heterocyclic group. When Z is an alkyl group, preferably it is a substituted or unsubstituted alkyl group having 1 to 20 carbon atoms, and more preferably having 1 to 8 carbon atoms. Examples of appropriate groups include ethyl, methyl, propyl, butyl, pentyl, hexyl, octyl, 2-ethylhexyl, decyl, dodecyl, hexadecyl, octadecyl, cyclohexyl, isopropyl and t-butyl groups.

The preferred aryl groups are substituted or unsubstituted and have from 6 to 20 carbon atoms. More preferably, the aryl groups have 6 to 10 carbon atoms and include, among others, phenyl and naphthyl groups. The alkylaryl groups are combinations of the alkyl and aryl groups described above, and preferably have from 7 to 20 carbon atoms and more preferably 7 to 11 carbon atoms. These groups may have substituent groups.

The heterocyclic groups are preferably substituted or unsubstituted 3 to 15-membered rings containing at least one atom selected from nitrogen, oxygen, sulfur, selenium and tellurium in the ring nucleus. More preferably, the heterocyclic groups are 5 to 6-membered rings with at least one atom, and preferably more than one atom, selected from nitrogen. Examples of heterocyclic groups include pyrrolidine, piperidine, pyridine, tetrahydrofuran, thiophene, oxazole, thiazole, imidazole, benzothiazole, benzoxazole, benzimidazole, selenazole, benzoselenazole, tellurazole, triazole, benzotriazole, tetrazole, oxadiazole, or thiadiazole rings. The preferred heterocyclic group is tetrazole.

$R_1$, $R_2$, $R_3$ and $R_4$ are individually selected from alkyl, aryl, alkylaryl, or heterocyclic groups, or one or both of $R_1$ and $R_2$ or $R_3$ and $R_4$ may combine to form a nitrogen containing heterocyclic ring. The definition of alkyl, aryl, alkylaryl, or heterocyclic groups for $R_1$, $R_2$, $R_3$ and $R_4$ are the same as for Z above.

In one preferred embodiment Z is a substituted or unsubstituted heterocyclic group, more preferably a substituted or unsubstituted 5 to 6-membered heterocyclic ring with at least one atom selected from nitrogen. In one embodiment Z is a tetrazole. In another preferred embodiment $R_1$, $R_2$, $R_3$ and $R_4$ are individually selected from substituted or unsubstituted alkyl groups having 1 to 8 carbon atoms.

Unless otherwise specifically stated, substituent groups which may be substituted on molecules herein include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be bonded to the remainder of the molecule by an atom of carbon, silicon, oxygen, nitrogen, phosphorous, or sulfur. Suitable substituents for A include, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin- 1-yl, 2-oxo-5-tetradecylpyrrolin-1-yl,N-methyltetradecanamido, N-succinimido, N-phthalimido, 2,5-dioxo- 1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecylphenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy. Preferred substituents are alkyl groups with 1 to 4 carbons.

Generally, the above groups and substituents thereof may include those having up to 48 carbon atoms, typically 1 to 36 carbon atoms and usually less than 24 carbon atoms, but greater numbers are possible depending on the particular substituents selected.

Examples of the Au(I) compounds of the invention include but are not limited to the following:

(A)

(B)

(C)

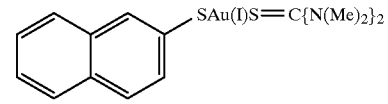

5

-continued (D) 2-phenanthryl—SAu(I)S=C{N(Ph)₂}₂

(E) 2-methylbenzothiazol-6-yl—SAu(I)S=C(NMeEt)₂

(F) 4-MeC₆H₄—SAu(I)S=C(NMeCH₂Ph)₂

(G) 3-phenanthryl—SAu(I)S=C(NMePhMe)₂

(H) 2-methyl-5-(...)-benzoic acid—SAu(I)S=C(NEtPhCl)₂ (with COOH)

(I) Me(CH₂)₄—SAu(I)S=C(NPhCH₂Ph)₂

(J) MeCH₂CH=CHCH₂—SAu(I)S=C(NButylPh)₂ (with MeO group)

Me-CH=CH-CH₂-OMe ... SAu(I)S=C(NMeEt)₂ (K)

(L) Me-CH=CH-CH=CH—SAu(I)S=C(NButylPh)₂

(M) 3,4-diMeC₆H₃—SAu(I)S=C{N(Me)₂}₂

6

-continued (N) 3-Cl-4-MeC₆H₃—SAu(I)S=C{N(Et)₂}₂

(O) 3-(NHAc)C₆H₄-tetrazol-5-yl—SAu(I)S=C{N(Me)₂}₂

(P) 3-Cl-5-(AcNH)C₆H₃-triazol-3-yl—SAu(I)S=C{N(PhCl)₂}₂

(Q) 4-ClC₆H₄-tetrazol-5-yl—SAu(I)S=C(NButylPhCl)₂

(R) 4-(AcNH)-3-(MeO)C₆H₃-triazol-3-yl—SAu(I)S=C(NCH₂PhPh)₂

(S) 3-(PhC(O)NH)C₆H₄-tetrazol-5-yl—SAu(I)S=C(NMeCH₂CH₂OH)₂

(T) 4,5-bis(4-ClC₆H₄)imidazol-2-yl—SAu(I)S=C(NEtCH₂CH₂OH)₂

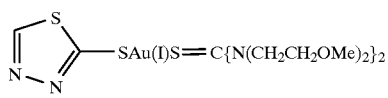
(U)

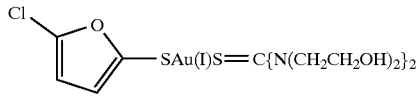
(V)

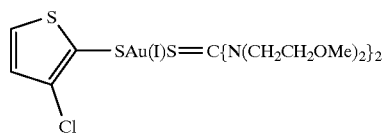
(W)

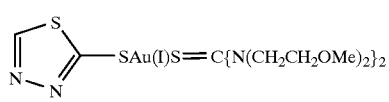
(X)

The Au(I) compounds are preferably synthesized in a gel dispersion. In one preparaion a mercaptan salt solution is added to a heated gelatin dispersion (approximately 45° C.). A solution of a Au(I) complex of a tetrasubstituted thiourea salt is then added to the gelatin dispersion and the mixture is rapidly stirred. Precipitation of the Au(I) compound will occur immediately upon the addition of the Au(I) thiourea complex to the gel dispersion. The gel dispersion should be stirred until the Au(I) compound is uniformly dispersed. The gel dispersion is then chilled until a jelled matrix is formed. The gel dispersion is then ready to be utilized in the photographic element.

Mercaptans are readily available materials. They are commercially available or they may be synthesized using standard methods known to those skilled in the art. Tetrasubstituted thioureas are also commercially available or may be prepared using standard methods.

Levels of the Au(I) compounds which may be utilized range from about 0.01 μmol to 10,000 μmol per silver mole; preferably from about 0.05 μmol to 1,000 μmol per silver mole; more preferably from about 0.1 μmol to 500 μmol per silver mole and most preferably from about 1 μmol to 50 μmol/Ag mole.

The photographic emulsions of this invention are generally prepared by precipitating silver halide crystals in a colloidal matrix by methods conventional in the art. The colloid is typically a hydrophilic film forming agent such as gelatin, alginic acid, or derivatives thereof.

The crystals formed in the precipitation step are washed and then chemically and spectrally sensitized by adding spectral sensitizing dyes and chemical sensitizers, and by providing a heating step during which the emulsion temperature is raised, typically from 40° C. to 70° C., and maintained for a period of time. The precipitation and spectral and chemical sensitization methods utilized in preparing the emulsions employed in the invention can be those methods known in the art.

Chemical sensitization of the emulsion typically employs sensitizers such as: sulfur-containing compounds, e.g., allyl isothiocyanate, sodium thiosulfate and allyl thiourea; reducing agents, e.g., polyamines and stannous salts; noble metal compounds, e.g., gold, platinum; and polymeric agents, e.g., polyalkylene oxides. As described, heat treatment is employed to complete chemical sensitization. Spectral sensitization is effected with a combination of dyes, which are designed for the wavelength range of interest within the visible or infrared spectrum. It is known to add such dyes both before and after heat treatment.

After spectral sensitization, the emulsion is coated on a support. Various coating techniques include dip coating, air knife coating, curtain coating and extrusion coating.

The Au(I) compounds may be added to the silver halide emulsion at any time during the preparation of the emulsion, i.e., during precipitation, during or before chemical sensitization or during final melting and co-mixing of the emulsion and additives for coating. Preferably, the emulsion is chemically sensitized in the presence of the Au(I) compounds. More preferably, these compounds are added after precipitation of the grains, and most preferably they are added before or during the heat treatment of the chemical sensitization step.

The Au(I) compounds may be introduced into the emulsion at the appropriate time by any of the various techniques known to those skilled in the art. Preferably they are added as a gel dispersion. One suitable method includes preparing a silver halide emulsion by precipitating silver halide grains in an aqueous colloidal medium to form an emulsion, digesting (heating) the emulsion, preferably at a temperature in the range of 40 to 80° C., and adding to the emulsion, either before or during heating, a gel dispersion of the Au(I) compound. In one preferred embodiment the emulsion is also sensitized with thiosulfate pentahydrate (hypo).

Conditions for sensitizing silver halide grains such a pH, pAg, and temperature are not particularly limited. The pH is generally about 1 to 9, preferably about 3 to 6, and pAg is generally about 5 to 12, preferably from about 7 to 10.

The Au(I) compounds may also be added to the vessel containing the aqueous gelatin salt solution before the start of the precipitation; or to a salt solution during precipitation. Other modes are also contemplated. Temperature, stirring, addition rates and other precipitation factors may be set within conventional ranges, by means known in the art, so as to obtain the desired physical characteristics.

The Au(I) compounds may be used in addition to any conventional sensitizers as commonly practiced in the art. Combinations of more than one Au(I) compound may be utilized.

The silver halide emulsions utilized in this invention may be comprised of any halide distribution. Thus, they may be comprised of silver bromoiodide, silver chloride, silver bromide, silver bromochloride, silver chlorobromide, silver iodochloride, silver iodobromide, silver bromoiodochloride, silver chloroiodobromide, silver iodobromochloride, and silver iodochlorobromide emulsions. In one embodiment silver bromoiodides with various morphologies and halide compositions may be utilized. Preferably, the silver halide emulsions utilized in this invention are predominantly silver chloride emulsions. By predominantly silver chloride, it is meant that the grains of the emulsion are greater than about 50 mole percent silver chloride. Preferably, they are greater than about 90 mole percent silver chloride; and optimally greater than about 95 mole percent silver chloride. These emulsions may contain iodides or bromides or both as the remainder of the total halide composition.

The silver halide emulsions can contain grains of any size and morphology. Thus, the grains may take the form of cubes, octahedrons, cubooctahedrons, or any of the other naturally occurring morphologies of cubic lattice type silver halide grains. Further, the grains may be irregular such as spherical grains or tabular grains. Grains having a tabular or cubic morphology are preferred. Tetradecahedral grains with {111} and {100} crystal faces may also be utilized. The Au(I) compounds may also be used in reversal systems having core shell silver halide emulsions.

The photographic emulsions may be incorporated into color negative (particularly color paper) or reversal photographic elements. The photographic element may also comprise a transparent magnetic recording layer such as a layer containing magnetic particles on the underside of a transparent support, as described in *Research Disclosure*, November 1992, Item 34390 published by Kenneth Mason Publications, Ltd., Dudley Annex, 12a North Street, Emsworth, Hampshire PO10 7DQ, ENGLAND. Typically, the element will have a total thickness (excluding the support) of from about 5 to about 30 microns. Further, the photographic elements may have an annealed polyethylene naphthalate film base such as described in Hatsumei Kyoukai Koukai Gihou No. 94-6023, published Mar. 15, 1994 (Patent Office of Japan and Library of Congress of Japan) and may be utilized in a small format system, such as described in *Research Disclosure*, June 1994, Item 36230 published by Kenneth Mason Publications, Ltd., Dudley Annex, 12a North Street, Emsworth, Hampshire PO10 7DQ, ENGLAND, and such as the Advanced Photo System, particularly the Kodak ADVANTIX films or cameras.

In the following Table, reference will be made to (1) *Research Disclosure*, December 1978, Item 17643, (2) *Research Disclosure*, December 1989, Item 308119, (3) *Research Disclosure*, September 1994, Item 36544, and (4) *Research Disclosure*, September 1996, Item 38957, all published by Kenneth Mason Publications, Ltd., Dudley Annex, 12a North Street, Emsworth, Hampshire PO10 7DQ, ENGLAND, the disclosures of which are incorporated herein by reference. The Table and the references cited in the Table are to be read as describing particular components suitable for use in the elements of the invention. The Table and its cited references also describe suitable ways of preparing, exposing, processing and manipulating the elements, and the images contained therein. Photographic elements and methods of processing such elements particularly suitable for use with this invention are described in *Research Disclosure*, February 1995, Item 37038, published by Kenneth Mason Publications, Ltd., Dudley Annex, 12a North Street, Emsworth, Hampshire PO10 7DQ, ENGLAND, the disclosure of which is incorporated herein by reference.

| Reference | Section | Subject Matter |
|---|---|---|
| 1 | I, II | Grain composition, |
| 2 | I, II, IX, X, XI, XII, XIV, XV | morphology and preparation. Emulsion preparation including |
| 3 & 4 | I, II, III, IX A & B | hardeners, coating aids, addenda, etc. |
| 1 | III, IV | Chemical sensitization and |
| 2 | III, IV | spectral sensitization/ |
| 3 & 4 | IV, V | desensitization |
| 1 | V | UV dyes, optical |
| 2 | V | brighteners, luminescent |
| 3 & 4 | VI | dyes |
| 1 | VI | Antifoggants and |
| 2 | VI | stabilizers |
| 3 & 4 | VII | |
| 1 | VIII | Absorbing and scattering |
| 2 | VIII, XIII, XVI | materials; Antistatic layers; matting agents |
| 3 & 4 | VIII, IX C & D | |
| 1 | VII | Image-couplers and image- |
| 2 | VII | modifying couplers; Wash- |
| 3 & 4 | X | out couplers; Dye stabilizers and hue modifiers |
| 1 | XVII | Supports |
| 2 | XVII | |
| 3 & 4 | XV | |
| 3 & 4 | XI | Specific layer arrangements |
| 3 & 4 | XII, XIII | Negative working emulsions; Direct positive emulsions |
| 2 | XVIII | Exposure |
| 3 & 4 | XVI | |
| 1 | XIX, XX | Chemical processing; |
| 2 | XIX, XX, XXII | Developing agents |
| 3 & 4 | XVIII, XIX, XX | |
| 3 & 4 | XIV | Scanning and digital processing procedures |

The photographic elements can be incorporated into exposure structures intended for repeated use or exposure structures intended for limited use, variously referred to as single use cameras, lens with film, or photosensitive material package units.

The photographic elements can be exposed with various forms of energy which encompass the ultraviolet, visible, and infrared regions of the electromagnetic spectrum as well as the electron beam, beta radiation, gamma radiation, X-ray, alpha particle, neutron radiation, and other forms of corpuscular and wave-like radiant energy in either noncoherent (random phase) forms or coherent (in phase) forms, as produced by lasers. When the photographic elements are intended to be exposed by X-rays, they can include features found in conventional radiographic elements.

The photographic elements are preferably exposed to actinic radiation, typically in the visible region of the spectrum, to form a latent image, and then processed to form a visible dye image. Development is typically followed by the conventional steps of bleaching, fixing, or bleach-fixing, to remove silver or silver halide, washing, and drying.

The following examples are intended to illustrate, but not limit, the invention.

EXAMPLE 1

Synthesis of bis-tetramethylthiourea Au(I)—
Compound ZZ

In a 4-L borosilicate beaker was placed 231.8 g of tetramethylthiourea and 300 mL of tetrafluoroboric acid (49%) in 2628 mL of distilled water. The mixture was warmed to approximately 50° C. when a clear solution was obtained. To this solution was added, with stirring, 110.4 g of potassium tetrachloroaurate in 500 mL of distilled water. The mixture was heated at 60° C. until a wine-red solution was obtained. The solution was cooled to 10° C. with occasional stirring. The precipitate was collected by filtration and then washed with 100 mL of ice-chilled water. After air-drying for about five minutes, the solid was re-suspended in 3.1 L of water which contained 1.0 g of tetramethylthiourea. The mixture was heated to about 60° C. until the solid dissolved. The process of cooling, filtering, washing and drying was repeated two more times. The final material was washed with 500 mL of ice-chilled water and then dried in an oven at 50° C. until constant weight was obtained. Yield of compound ZZ was about 85%. Au was analyzed at 35.8% (calculated at 35.87%).

Synthesis of 1-(3-acetamidophenyl)-5-mercaptotetrazole tetramethylthiourea Au(I)-Compound O To a solution of ZZ (1.5 g) in warm distilled water (200 mL) was added with stirring a solution of sodium salt of 1-(3-acetamidophenyl)-5-mercaptotetrazole (0.704 g) in 20 mL of distilled water. The mixture was filtered, washed with water and then dried to constant weight. The weight of the solid was 1.10 g or a yield of 71%. Component analysis of compound yielded the following data: Au:34.43%, C:29.46%, S:11.08%, H:3.58%, N:17.05. The calculated values are: Au:34.96%, C:29.84%, S:11.38%, H:3.58%, N:17.40. Thermogravimetric analysis, infrared analysis and X-ray diffraction patterns were all consistent with the structure of Compound O.

Synthesis of Compound O in a Gelatin Dispersion

A solution of sodium salt of 1-(3-acetamidophenyl)-5-mercaptotetrazole (2.349 g) was made by dissolving the solid in 160 mL of distilled water. This solution was added to a dispersion made with 307.2 g of gelatin (12.5%) in a 4 L beaker at 45° C. To this gelatin dispersion was added slowly with stirring, a solution of ZZ (5.0 g) in warm distilled water (525 g). The mixture was stirred rapidly for another two minutes before it was chilled to 25° C. Finally the temperature was lowered to 10° C. without further stirring. The weight of the dispersion was 991.2 g with gold calculated at 1.80 g per Kg of gel dispersion or 5.15g of O per Kg of dispersion.

Preparation of Sodium Salt of 1-(3-acetamidophenyl)-5-mercaptotetrazole(QQ) and tetramethylthiourea (TT) in a Gelatin Dispersion A solution of QQ, (2.34 g in 160 mL of distilled water) was added to a gelatin dispersion (307.2 g of 12.5% gelatin) in a 4 L beaker at 45° C. To this gelatin dispersion was added slowly with stirring a solution of TT (2.42 g) in warm distilled water (528 g). The mixture was stirred rapidly for another two minutes before it was chilled to 25° C. Finally the temperature was lowered to 10° C. without further stirring. The weight of the dispersion was 982.0 g.

EXAMPLE 2

In accordance with the present invention, a 0.3 mole cubic negative silver chloride emulsion was sensitized with p-glutaramidophenyl disulfide (10 mg/Ag mol), hypo (7.42 mg/Ag mol) and with sensitizer O and comparison compounds QQ and TT as indicated in Table 1 at 40° C. The emulsion was heated to 60° C. at a rate of 20° C. per 17 minutes and then held at this temperature for 52 minutes. During this time, 1-(3-acetamidophenyl)-5-mercaptotetrazole (297 mg/Ag mol), potassium hexachloroiridate (0.121 mg/Ag mol) and potassium bromide (1359 mg/Ag mol) were added. The emulsion was cooled down to 40° C. at a rate of 20° C. per 17 minutes. At this time, a red spectral sensitizing dye, anhydro-3-ethyl-9,11-neopentylene-3'-(3-sulfopropyl)thiadicarbocyanine hydroxide (12 mg/Ag mol), was added and the pH of the emulsion was adjusted to 6.0. An emulsion thus sensitized also contained a cyan dye-forming coupler 2-(alpha (2,4-di-tert-amyl-phenoxy)butyramido)-4,6-dichloro-5-ethyl phenol (0.42 g/m$^2$) in di-n-butyl phthalate coupler solvent (0.429 g/m$^2$) and gelatin (1.08g/m$^2$). The emulsion (0.18 g Ag/m$^2$) was coated on a resin coated paper support and 1.076 g/m$^2$ gel overcoat was applied as a protective layer along with the hardener bis (vinylsulfonyl) methyl ether in an amount of 1.8% of the total gelatin weight.

The coatings were given a 0.1 second exposure, using a 0–3 step tablet (0.15 increments) with a tungsten lamp designed to stimulate a color negative print exposure source. This lamp had a color temperature of 3000K, log lux 2.95, and the coatings were exposed through a combination of magenta and yellow filters, a 0.3 ND (Neutral Density), and a UV filter. The processing consisted of a color development (45 sec, 35° C.), bleach-fix (45 sec, 35° C.) and stabilization or water wash (90 sec, 35° C.) followed by drying (60 sec, 60° C.). The chemistry used in the Colenta processor consisted of the following solutions:

| Developer: | | |
|---|---|---|
| Lithium salt of sulfonated polystyrene | 0.25 | mL |
| Triethanolamine | 11.0 | mL |
| N,N-diethylhydroxamine (85% by wt.) | 6.0 | mL |
| Potassium sulfite (45% by wt.) | 0.5 | mL |
| Color developing agent (4-(N-ethyl-N-2-methanesulfonyl aminoethyl)-2-methyl-phenylenediaminesesquisulfate monohydrate | 5.0 | g |
| Stilbene compound stain reducing agent | 2.3 | g |
| Lithium sulfate | 2.7 | g |
| Potassium chloride | 2.3 | g |
| Potassium bromide | 0.025 | g |
| Sequestering agent | 0.8 | mL |
| Potassium carbonate | 25.0 | g |
| Water to total of 1 liter, pH adjusted to 10.12 | | |
| Bleach-fix | | |
| Ammonium sulfite | 58 | g |
| Sodium thiosulfate | 8.7 | g |
| Ethylenediaminetetracetic acid ferric ammonium salt | 40 | g |
| Acetic acid | 9.0 | mL |
| Water to total 1 liter, pH adjusted to 6.2 | | |
| Stabilizer | | |
| Sodium citrate | 1 | g |
| Water to total 1 liter, pH adjusted to 7.2. | | |

The speed taken at the 1.0 density point of the D log E curve was taken as a measure of the sensitivity of the emulsion. Dmin was measured as the minimum density above zero. Toe at 0.5 was taken as the density at 0.5 log E fast of the density point of 1.0. Toe at 0.3 was taken as the density at 0.3 log E fast of the density point of 1.0. Shoulder was taken as the density at 0.5 log E slow of the density point of 1.0. Gamma is the slope of the line between the density points that are 0.3 log E faster and 0.3 log E slower than the density point at 1.0. Dmax is the maximum density of the D log E curve.

It can be seen in Table 1 that Samples 1 (without O), 2, and 3 (without O but with control compounds without gold, QQ and TT) all have lower speed and show little sensitization.

TABLE 1

| Sample | Compound | μmol Ag mol | Spd | Dmin | 0.5 Toe | 0.3 Toe | Shldr | Gamma | Dmax |
|---|---|---|---|---|---|---|---|---|---|
| 1 (comparison) | none | 0 | 66 | 0.099 | 0.401 | 0.709 | 1.260 | 0.918 | 1.773 |
| 2 (comparison) | QQ TT | 0.5 X | 69 | 0.098 | 0.369 | 0.685 | 1.225 | 0.900 | 1.741 |
| 3 (comparison) | QQ—TT | 2.5 X | 70 | 0.100 | 0.171 | 0.354 | 1.470 | 1.860 | 2.024 |
| 4 (invention) | O | 0.5 X | 111 | 0.096 | 0.340 | 0.578 | 1.405 | 1.378 | 2.126 |
| 5 (invention) | O | X | 150 | 0.113 | 0.155 | 0.318 | 2.004 | 2.809 | 2.749 |
| 6 (invention) | O | 1.5 X | 149 | 0.114 | 0.158 | 0.322 | 2.006 | 2.806 | 2.732 |
| 7 (invention) | O | 2 X | 143 | 0.106 | 0.145 | 0.302 | 2.022 | 2.867 | 2.767 |
| 8 (invention) | O | 2.5 X | 137 | 0.101 | 0.154 | 0.316 | 1.986 | 2.783 | 2.640 |
| 9 (invention) | O | 3 X | 131 | 0.102 | 0.168 | 0.345 | 1.892 | 2.579 | 2.658 |

X = 27.27 μmol per Ag mol

Samples of the present invention (4–9) which contain compound O showed much enhanced sensitivity. More specifically, Sample 7 had the best combination of speed, toes (lower values indicate sharper toe), high shoulder and contrast.

EXAMPLE 3

In another practice of the invention, a 0.3 mol of a negative silver chloride emulsion was sensitized with a green spectral sensitizing dye, 5-chloro-2-[2-[[5-phenyl-3-(3-sulfobutyl)-2(3H)-benzoxazolylidene]methyl]-1-butenyl]-3-(3-sulfopropyl)-benzoxazolium sodium salt (379.45 mg/Ag mol), 0.28 mg/Ag mol of sodium thiosulfate pentahydrate (hypo), and with compound O, ZZ or compounds QQ and TT at levels indicated in Table 2 at 40° C. The emulsion was heated to 60° C. at a rate of 10° C. per 6 minutes and then held at this temperature for 40 minutes. The emulsion was cooled to 40° C. at a rate of 10° C. per 6 minutes. At 40° C., solutions of 1-(3-acetamidophenyl)-5-mercaptotetrazole (200 mg/Ag mol) and potassium bromide (795 mg/Ag mol) were added to the emulsion. This emulsion was mixed further with a green dye-forming coupler 7-chloro-6-(1,1 -dimethylethyl)-3-[3-(dodecylsulfonyl) propyl]-1H-pyrazolo[5,1-c]-1,2,4-triazole ( 0.018 g/m²) in di-n-butylphthalate coupler solvent and gelatin. The emulsion (0.102 g Ag/m²) was coated on a resin coated paper support and an overcoat applied as a protective layer along with the hardener bis (vinylsulfonyl) methyl ether in an amount of 1.8% of the total gelatin weight. The emulsion (0.102 g Ag/m²) was coated on a resin coated paper support and an overcoat applied as a protective layer along with the hardener bis (vinylsulfonyl) methyl ether in an amount of 1.8% of the total gelatin weight. The coatings were exposed and processed as for Example 2.

The data in Table 2 show again that samples containing only the control compounds without gold, (11, and 12) have no sensitizing effect relative to the coating with no sensitizer (sample 10). Samples containing the combination of compound O and hypo (samples 15, 16) show speeds higher than the coatings with the comparison sensitizer ZZ (samples 13,14).

TABLE 2

| Samples | Compound | μmol Ag mol | hypo | Spd | Dmin | 0.5 Toe | 0.3 Toe | Gamma | Shldr | Dmax |
|---|---|---|---|---|---|---|---|---|---|---|
| 10 (comparison) | none | — | Y | 80 | 0.096 | 0.207 | 0.397 | 2.516 | 1.907 | 2.540 |
| 11 (comparison) | QQ,TT | X | Y | 80 | 0.088 | 0.181 | 0.372 | 2.612 | 1.939 | 2.537 |
| 12 (comparison) | QQ,TT | 2X | Y | 80 | 0.096 | 0.207 | 0.382 | 2.568 | 1.923 | 2.578 |
| 13 (comparison) | ZZ | X | Y | 104 | 0.099 | 0.609 | 0.740 | 1.378 | 1.567 | 2.623 |
| 14 (comparison) | ZZ | 2X | Y | 175 | 0.103 | 0.176 | 0.359 | 2.559 | 1.894 | 2.704 |
| 15 (invention) | O | X | Y | 166 | 0.102 | 0.222 | 0.437 | 1.895 | 1.574 | 2.611 |
| 16 (invention) | O | 2X | Y | 178 | 0.100 | 0.163 | 0.343 | 2.676 | 1.948 | 2.583 |
| 17 (comparison) | none | 0 | N | 76 | 0.098 | 0.179 | 0.358 | 2.737 | 2.000 | 2.651 |
| 18 (comparison) | ZZ | X | N | 81 | 0.096 | 0.247 | 0.397 | 2.596 | 1.954 | 2.556 |
| 19 (comparison) | ZZ | 3X | N | 78 | 0.099 | 0.206 | 0.387 | 2.619 | 1.959 | 2.591 |
| 20 (invention) | O | X | N | 84 | 0.100 | 0.231 | 0.398 | 2.577 | 1.944 | 2.604 |
| 21 (invention) | O | 3X | N | 81 | 0.095 | 0.227 | 0.386 | 2.630 | 1.965 | 2.611 |

X = 7.02 μmol per Ag mol

For the emulsions sensitized without hypo, the invention Samples (20, 21), have a higher speed than the comparison emulsion sensitized with ZZ (Samples 18,19).

The invention has been described in detail with particular reference to certain preferred embodiments thereof, but it will be understood that variations and modifications can be effected within the spirit and scope of the invention.

What is claimed is:

1. A silver halide photographic element comprising a support and a silver halide emulsion layer, the emulsion layer comprising a Au(I) compound having the formula

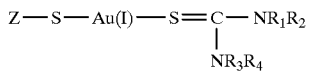

wherein Z is a substituted or unsubstituted alkyl, aryl, alkylaryl, or heterocyclic group; and $R_1$, $R_2$, $R_3$ and $R_4$ are independently substituted or unsubstituted alkyl, aryl, alkylaryl, or heterocyclic groups, or one or both of $R_1$ and $R_2$, or $R_3$ and $R_4$, may independently combine to form a substituted or unsubstituted nitrogen containing ring with the nitrogen to which they are attached.

2. The photographic element of claim 1 wherein Z is a substituted or unsubstituted alkyl group having 1 to 20 carbon atoms, a substituted or unsubstituted aryl group having from 6 to 20 carbon atoms, a substituted or unsubstituted alkylaryl group having from 7 to 20 carbon atoms, or a substituted or unsubstituted 3 to 15-membered heterocyclic ring with at least one atom selected from nitrogen, oxygen, sulfur, selenium or tellurium.

3. The photographic element of claim 2 wherein Z is a substituted or unsubstituted alkyl group having 1 to 8 carbon atoms, a substituted or unsubstituted aryl group having from 6 to 10 carbon atoms, a substituted or unsubstituted alkylaryl group having from 7 to 11 carbon atoms, or a substituted or unsubstituted 5 to 6-membered heterocyclic ring with at least one atom selected from nitrogen.

4. The photographic element of claim 3 wherein Z is a substituted or unsubstituted 5 to 6-membered heterocyclic ring with at least one atom selected from nitrogen.

5. The photographic element of claim 1 wherein $R_1$, $R_2$, $R_3$ and $R_4$ are independently substituted or unsubstituted alkyl groups having 1 to 20 carbon atoms, substituted or unsubstituted aryl groups having from 6 to 20 carbon atoms, substituted or unsubstituted alkylaryl groups having from 7 to 20 carbon atoms, substituted or unsubstituted 3 to 15-membered heterocyclic rings with at least one atom selected from nitrogen, oxygen, sulfur, selenium or tellurium; or one or both $R_1$ and $R_2$, or $R_3$ and $R_4$, may independently combine to form a substituted or unsubstituted 3 to 15-membered nitrogen containing ring with the nitrogen to which they are attached.

6. The photographic element of claim 5 wherein $R_1$, $R_2$, $R_3$ and $R_4$ are independently substituted or unsubstituted alkyl groups having 1 to 8 carbon atoms, substituted or unsubstituted aryl groups having from 6 to 10 carbon atoms, substituted or unsubstituted alkylaryl groups having from 7 to 11 carbon atoms, or substituted or unsubstituted 5 to 6-membered heterocyclic rings with at least one atom selected from nitrogen, oxygen, sulfur, selenium or tellurium; or one or both of $R_1$ and $R_2$, or $R_3$ and $R_4$, may independently combine to form a substituted or unsubstituted 5 to 6-membered nitrogen containing ring with the nitrogen to which they are attached.

7. The photographic element of claim 6 wherein $R_1$, $R_2$, $R_3$ and $R_4$ are independently substituted or unsubstituted alkyl groups having 1 to 8 carbon atoms.

8. The photographic element of claim 3 wherein $R_1$, $R_2$, $R_3$ and $R_4$ are independently substituted or unsubstituted alkyl groups having 1 to 8 carbon atoms, substituted or unsubstituted aryl groups having from 6 to 10 carbon atoms, substituted or unsubstituted alkylaryl groups having from 7 to 11 carbon atoms, or substituted or unsubstituted 5 to 6-membered heterocyclic rings with at least one atom selected from nitrogen, oxygen, sulfur, selenium or tellurium; or one or both of $R_1$ and $R_2$ or $R_3$ and $R_4$, may independently combine to form a substituted or unsubstituted 5 to 6-membered nitrogen containing ring with the nitrogen to which they are attached.

9. The photographic element of claim 4 wherein $R_1$, $R_2$, $R_3$ and $R_4$ are independently substituted or unsubstituted alkyl groups having 1 to 8 carbon atoms.

10. The photographic element of claim 1 wherein the silver halide emulsion is greater than 95 mole % silver chloride.

11. The photographic element of claim 1 wherein the amount of the Au(I) compound contained in the silver halide emulsion is from 0.1 $\mu$mol to 500 $\mu$mol per mole of silver.

12. The photographic element of claim 1 wherein the amount of the Au(I) compound contained in the silver halide emulsion is from 1 $\mu$mol to 50 $\mu$mol per mole of silver.

13. A silver halide photographic element comprising a support and a silver halide emulsion layer, the emulsion layer having been chemically sensitized in the presence of an Au(I) compound having the formula

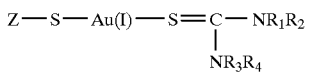

wherein Z is a substituted or unsubstituted alkyl, aryl, alkylaryl, or heterocyclic group; and $R_1$, $R_2$, $R_3$ and $R_4$ are independently substituted or unsubstituted alkyl, aryl, alkylaryl, or heterocyclic groups, or one or both of $R_1$ and $R_2$ or $R_3$ and $R_4$, may independently combine to form a substituted or unsubstituted nitrogen containing ring with the nitrogen to which they are attached.

14. The photographic element of claim 13 wherein Z is a substituted or unsubstituted alkyl group having 1 to 20 carbon atoms, a substituted or unsubstituted aryl group having from 6 to 20 carbon atoms, a substituted or unsubstituted alkylaryl group having from 7 to 20 carbon atoms, or a substituted or unsubstituted 3 to 15-membered heterocyclic ring with at least one atom selected from nitrogen, oxygen, sulfur, selenium or tellurium.

15. The photographic element of claim 14 wherein Z is a substituted or unsubstituted alkyl group having 1 to 8 carbon atoms, a substituted or unsubstituted aryl group having from 6 to 10 carbon atoms, a substituted or unsubstituted alkylaryl group having from 7 to 11 carbon atoms, or a substituted or unsubstituted 5 to 6-membered heterocyclic ring with at least one atom selected from nitrogen.

16. The photographic element of claim 15 wherein Z is a substituted or unsubstituted 5 to 6-membered heterocyclic ring with at least one atom selected from nitrogen.

17. The photographic element of claim 13 wherein $R_1$, $R_2$, $R_3$ and $R_4$ are independently substituted or unsubstituted alkyl groups having 1 to 20 carbon atoms, substituted or unsubstituted aryl groups having from 6 to 20 carbon atoms, substituted or unsubstituted alkylaryl groups having from 7 to 20 carbon atoms, or substituted or unsubstituted 3 to 15-membered heterocyclic rings with at least one atom selected from nitrogen, oxygen, sulfur, selenium or tellurium; or one or both of $R_1$ and $R_2$ or $R_3$ and $R_4$, may independently combine to form a substituted or unsubstituted 3 to 15-membered nitrogen containing ring with the nitrogen to which they are attached.

18. The photographic element of claim 17 wherein $R_1$, $R_2$, $R_3$ and $R_4$ are independently substituted or unsubstituted alkyl groups having 1 to 8 carbon atoms, substituted or unsubstituted aryl groups having from 6 to 10 carbon atoms, substituted or unsubstituted alkylaryl groups having from 7 to 11 carbon atoms, or substituted or unsubstituted 5 to 6-membered heterocyclic rings with at least one atom selected from nitrogen, oxygen, sulfur, selenium or tellurium; or one or both of $R_1$ and $R_2$ or $R_3$ and $R_4$, may independently combine to form a substituted or unsubstituted 5 to 6-membered nitrogen containing ring with the nitrogen to which they are attached.

19. The photographic element of claim 18 wherein $R_1$, $R_2$, $R_3$ and $R_4$ are independently substituted or unsubstituted alkyl groups having 1 to 8 carbon atoms.

20. The photographic element of claim 15 wherein $R_1$, $R_2$, $R_3$ and $R_4$ are independently substituted or unsubstituted alkyl groups having 1 to 8 carbon atoms, substituted or unsubstituted aryl groups having from 6 to 10 carbon atoms, substituted or unsubstituted alkylaryl groups having from 7 to 11 carbon atoms, or substituted or unsubstituted 5 to 6-membered heterocyclic rings with at least one atom selected from nitrogen, oxygen, sulfur, selenium or tellurium; or one or both of $R_1$ and $R_2$ or $R_3$ and $R_4$, may independently combine to form a substituted or unsubstituted 5 to 6-membered nitrogen containing ring with the nitrogen to which they are attached.

21. The photographic element of claim 20 wherein $R_1$, $R_2$, $R_3$ and $R_4$ are independently substituted or unsubstituted alkyl groups having 1 to 8 carbon atoms.

22. The photographic element of claim 13 wherein the silver halide emulsion is greater than 95 mole % silver chloride.

23. The photographic element of claim 13 wherein the amount of the Au(I) compound contained in the silver halide emulsion is from 0.1 μmol to 500 μmol per mole of silver.

24. A method of preparing a silver halide emulsion comprising precipitating silver halide grains in an aqueous colloidal medium to form an emulsion, heating the emulsion, and adding to the emulsion, either before or during heating, a Au(I) compound having the formula

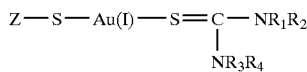

wherein Z is a substituted or unsubstituted alkyl, aryl, alkylaryl, or heterocyclic group; and $R_1$, $R_2$, $R_3$ and $R_4$ are independently substituted or unsubstituted alkyl, aryl, alkylaryl, or heterocyclic groups, or one or both of $R_1$ and $R_2$ or $R_3$ and $R_4$, may independently combine to form a substituted or unsubstituted nitrogen containing ring with the nitrogen to which they are attached.

25. The method of claim 24 wherein Z is a substituted or unsubstituted alkyl group having 1 to 8 carbon atoms, a substituted or unsubstituted aryl group having from 6 to 10 carbon atoms, a substituted or unsubstituted alkylaryl group having from 7 to 11 carbon atoms, or a substituted or unsubstituted 5 to 6-membered heterocyclic ring with at least one atom selected from nitrogen and wherein $R_1$, $R_2$, $R_3$ and $R_4$ are independently substituted or unsubstituted alkyl groups having 1 to 8 carbon atoms, substituted or unsubstituted aryl groups having from 6 to 10 carbon atoms, substituted or unsubstituted alkylaryl groups having from 7 to 11 carbon atoms, or substituted or unsubstituted 5 to 6-membered heterocyclic rings with at least one atom selected from nitrogen, oxygen, sulfur, selenium or tellurium; or one or both of $R_1$ and $R_2$ or $R_3$ and $R_4$, may independently combine to form a substituted or unsubstituted 5 to 6-membered nitrogen containing ring with the nitrogen to which they are attached.

26. The method of claim 24 wherein the silver halide emulsion is greater than 95 mole % silver chloride.

27. The method of claim 24 wherein the amount of the Au(I) compound added to the silver halide emulsion is from 0.1 μmol to 500 μmol per mole of silver.

28. The method of claim 24 wherein hypo is added to the emulsion either before or during heating.

29. A Au(I) compound having the formula

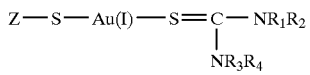

wherein Z is a substituted or unsubstituted alkyl, aryl, alkylaryl, or heterocyclic group; and $R_1$, $R_2$, $R_3$ and $R_4$ are independently substituted or unsubstituted alkyl, aryl, alkylaryl, or heterocyclic groups, or one or both of $R_1$ and $R_2$, or $R_3$ and $R_4$, may independently combine to form a substituted or unsubstituted nitrogen containing ring with the nitrogen to which they are attached.

30. The compound of claim 29 wherein Z is a substituted or unsubstituted alkyl group having 1 to 8 carbon atoms, a substituted or unsubstituted aryl group having from 6 to 10 carbon atoms, a substituted or unsubstituted alkylaryl group having from 7 to 11 carbon atoms, or a substituted or unsubstituted 5 to 6-membered heterocyclic ring with at least one atom selected from nitrogen and wherein $R_1$, $R_2$, $R_3$ and $R_4$ are independently substituted or unsubstituted alkyl groups having 1 to 8 carbon atoms, substituted or unsubstituted aryl groups having from 6 to 10 carbon atoms, substituted or unsubstituted alkylaryl groups having from 7 to 11 carbon atoms, or substituted or unsubstituted 5 to 6-membered heterocyclic rings with at least one atom selected from nitrogen, oxygen, sulfur, selenium or tellurium; or one or both of $R_1$ and $R_2$, or $R_3$ and $R_4$, may independently combine to form a substituted or unsubstituted 5 to 6-membered nitrogen containing ring with the nitrogen to which they are attached.

* * * * *